(12) United States Patent
Irion et al.

(10) Patent No.: US 8,189,062 B2
(45) Date of Patent: May 29, 2012

(54) IMAGE PICK-UP MODULE AND METHOD FOR ASSEMBLING SUCH AN IMAGE PICK-UP MODULE

(75) Inventors: Klaus M. Irion, Liptingen (DE); Peter Schwarz, Tuttlingen (DE); Mark Kocher, Sindelfingen (DE); Ulrich Kehr, Wurmlingen (DE)

(73) Assignee: Karl Storz GmbH & Co, KG (DE)

( * ) Notice: Subject to any disclaimer, the term of this patent is extended or adjusted under 35 U.S.C. 154(b) by 824 days.

(21) Appl. No.: 12/243,197

(22) Filed: Oct. 1, 2008

(65) Prior Publication Data

US 2009/0027491 A1 Jan. 29, 2009

Related U.S. Application Data

(60) Division of application No. 09/994,178, filed on Nov. 26, 2001, now Pat. No. 7,773,122, which is a continuation of application No. PCT/EP00/04792, filed on May 25, 2000.

(30) Foreign Application Priority Data

May 27, 1999 (DE) .................................. 199 24 189

(51) Int. Cl.
*H04N 5/228* (2006.01)
(52) U.S. Cl. ...................... 348/222.1; 348/373; 348/374; 348/45; 348/65
(58) Field of Classification Search ............... 348/222.1, 348/373–375, 45–65, 72; 600/101, 109–112
See application file for complete search history.

(56) References Cited

U.S. PATENT DOCUMENTS

| | | | |
|---|---|---|---|
| 4,741,327 A | | 5/1988 | Yabe |
| 4,757,805 A | | 7/1988 | Yabe |
| 4,779,130 A | * | 10/1988 | Yabe ............................. 348/76 |

(Continued)

FOREIGN PATENT DOCUMENTS

DE 3720624 A1 1/1988

(Continued)

OTHER PUBLICATIONS

International Search Report, PCT/EP00/04792, Aug. 21, 2000, 3 Pages.

*Primary Examiner* — Yogesh Aggarwal
(74) *Attorney, Agent, or Firm* — St. Onge Steward Johnston & Reens LLC

(57) ABSTRACT

An image pick-up module comprises an electronic image sensor, single-piece circuit board electrically bonded to the image sensor, and at least one cable electrically bonded and leading away from the circuit board. The circuit board has at least three sections, first and second section extending in relation to the other and obliquely or crosswise to the image sensor, and third section arranged between first and second section. The image sensor is arranged on the circuit board opposite the third section. In a method for assembling the image pick-up module, the circuit board has the form of a planar board blank comprising at least three sections folded along flexible connecting sections whereby the at least one cable is bonded to the board, and the board folds whereby a third section is located between first and second section, and the image sensor is bonded to the circuit board opposite the third section.

15 Claims, 6 Drawing Sheets

U.S. PATENT DOCUMENTS

| | | | |
|---|---|---|---|
| 5,166,787 A | 11/1992 | Irion | |
| 5,220,198 A * | 6/1993 | Tsuji | 257/731 |
| 5,231,248 A | 7/1993 | Shah | |
| 5,454,366 A | 10/1995 | Ito et al. | |
| 5,506,401 A | 4/1996 | Segawa et al. | |
| 5,754,313 A * | 5/1998 | Pelchy et al. | 358/473 |
| 5,786,589 A | 7/1998 | Segawa et al. | |
| 5,857,963 A | 1/1999 | Pelchy et al. | |
| 6,195,261 B1 | 2/2001 | Babutzka et al. | |

FOREIGN PATENT DOCUMENTS

| | | |
|---|---|---|
| DE | 69204842 T2 | 5/1996 |
| DE | 69408558 T2 | 7/1998 |
| DE | 19924189 A1 | 1/2001 |
| JP | 63254869 A | 10/1988 |
| JP | 5115436 A | 5/1993 |
| JP | 6178757 A | 6/1994 |

* cited by examiner

IMAGE PICK-UP MODULE AND METHOD FOR ASSEMBLING SUCH AN IMAGE PICK-UP MODULE

CROSS-REFERENCE TO RELATED APPLICATIONS

The present application is divisional of U.S. patent application Ser. No. 09/994,178 filed on Nov. 26, 2001 now U.S. Pat. No. 7,773,122, which is a continuation of International Patent Application PCT/EP2000/04792 filed on May 25, 2000, which designates the United States and which claims priority of German patent application 199 24 189 filed on May 27, 1999.

FIELD OF THE INVENTION

The present invention relates to an image pick-up module, especially for an endoscope, comprising an electronic image sensor, a single-piece circuit board which is electrically bonded to the image sensor and to which is further electrically bonded at least one cable leading away from the circuit board, the circuit board having at least three sections, with a first section and a second section extending in spaced relation one to the other and obliquely or crosswise to the image sensor and a third section being arranged between the first and the second sections.

BACKGROUND OF THE INVENTION

The invention further relates to a method for assembling an image pick-up module, wherein an electronic image sensor is electrically bonded to a single-piece circuit board and the circuit board is electrically bonded to at least one cable leading away from the circuit board.

An image pick-up module of the before-mentioned kind is known from U.S. Pat. No. 5,220,198.

Electronic image pick-up modules of this kind find general application in the field of video recording. In addition to the use in video cameras, such electronic image pick-up modules have recently been employed in maximally miniaturized applications, especially in endoscopes for technical or medical purposes. Such endoscopes, or video endoscopes, have been disclosed, for example, in U.S. Pat. No. 5,754,313 and U.S. Pat. No. 5,166,787.

An image pick-up module comprises, generally, an electronic image sensor or image pick-up, by which light imaged on it is converted into an electric signal. Such electronic image sensors are generally implemented in CCD or CMOS technology. Further, the image pick-up module comprises at least one circuit board which accommodates the signal electronics, or at least part of the signal electronics, for the image sensor. The signal electronics comprise circuits that are implemented on the circuit board by electronic components or in the form of printed circuits. In addition, the image pick-up module comprises at least one cable, leading away from the circuit board, which is connected, at a point remote from the image pick-up module, to an electronic control and signal processing system for processing the electric signals received from the image pick-up module to reproduce the image received by the image sensor on an image reproduction unit, such as a display or a monitor.

As a rule, however, the circuit board is bonded not only to a single cable but to a system of several, partially coaxial, cables which form the electric signal transmission system between the image pick-up module and the electronic control and signal processing system.

It is only due to the miniaturization of the image sensors and the progress achieved in microtechnology that the use of such image pick-up modules in endoscopes has become possible. The image pick-up module is arranged in an endoscope in the distal tip of the endoscope shaft, i.e. the tip facing the patient, as is described in the before-mentioned U.S. Pat. No. 5,166,787. The image pick-up module replaces in this case the optical image transmission system used in "classical" endoscopes, which consist of a plurality of lenses arranged in series. Instead of transmitting the distally received image to the proximal end, i.e. the end remote from the patient, by means of an optical imaging lens system, an image pick-up module converts the optical light signals to electric signals and transmits them to the proximal end, via at least one cable or, as a rule, a cable system. The use of electronic image pick-up modules instead of optically transmitting lens systems provides the advantage, according to the before-mentioned US Patent Specification, that the image pick-up module need not be installed rigidly in the distal tip of the endoscope shaft, but can be mounted movably in that tip so that once the endoscope has been introduced into the cavity to be inspected, the image pick-up module can be pushed out distally from the shaft or can be swung out laterally from the shaft, with the effect that on the one hand a larger area can be viewed through the movable image sensor while on the other hand the endoscope shaft is released so that instruments can be introduced through the shaft into the cavity, for example. In addition, a telescope-like extension of the endoscope is also imaginable.

It is always a requirement with endoscopes that the cross-section of the outer contour of the shaft be as small as possible. Accordingly, in order to be accommodated in such a shaft, the image pick-up modules used must have the smallest possible outer cross-section. The shaft diameter of a video endoscope for medical purposes, for example, is as small as a few millimeters (<10 mm). This means that the dimensions of the miniaturized image pick-up modules should be as small as ever possible (if possible #6 mm). While presently existing image sensors, designed in so-called "case-less" configuration and with flexible connecting fingers, succeed increasingly in meeting these demands, the problem of making the overall structure of the image pick-up modules as small as possible continues to exist.

The image pick-up module known from U.S. Pat. No. 5,754,313 comprises two separate, i.e. not a single-piece, circuit boards for bonding the image sensor, which two circuit boards accommodate, in customary fashion, electronic miniature components and serve for bonding the cable system. The circuit boards extend in parallel one to the other and substantially at a right angle relative to the image pick-up surface of the image sensor. Since the signal electronics accommodated on the two circuit boards cannot function independently, an electric connection, for example in the form of lines, or a connecting circuit board must be additionally integrated which constitutes a further increase of the assembly effort connected with the image pick-up module. In addition, bonding the cables and the electric components between the boards has been found to present a problem. Further, the cables leading away from the circuit board are bonded to the circuit board on an outer surface of the latter in the case of this image pick-up module. Given the diameter of the different cables, which in part may be coaxial lines in which case they exhibit a corresponding thickness, the described structure of the known image pick-up module results in a cross-sectional diameter greater than the cross-sectional diameter defined by the image sensor.

Another problem presenting itself when such image pick-up modules are used in video endoscopes consists in that the one or the several cables, that lead away from the circuit board, may be exposed to tensile strain, especially in the case of flexible video endoscopes or when a deflection mechanism is provided for moving the image pick-up module, as described in U.S. Pat. No. 5,166,787, or during installation of the module in the endoscope shaft. Here again, the image pick-up module known from U.S. Pat. No. 5,754,313 has been found to be disadvantageous insofar as the strain relief device would have to be provided either around the bonding area of the cables on the two circuit boards, which would further disadvantageously increase the cross-sectional diameter of that known image pick-up module, or else would have to be provided at the proximal end of the circuit boards with the result that the length of the image pick-up module would be additionally increased in an undesirable way, which is a problem especially with flexible endoscopes where the stiff distal jaw parts should be kept as short as possible.

The image pick-up module known from the before-mentioned U.S. Pat. No. 5,220,198, from which the present invention starts, comprises a single-piece circuit board having three sections forming in this case the shape of a U; the present invention is, however, not restricted to that embodiment. The two sections, that are bonded to the image sensor, extend one parallel to other, the image sensor being fastened on the third section which extends crosswise to the two other sections. Accordingly, the circuit board is open on the side opposite the image sensor. This image pick-up module also provides the disadvantage that no strain relief is provided for the cables leading away from the circuit board. Under tensile strain conditions, there is therefore a risk for the cables leading away from the circuit board that the one or the several cables may be torn off the circuit board under strain.

Now, it is an object of the present invention to improve an image pick-up module of the before-mentioned kind in such a way that strain relief is provided, with small constructional effort, for the at least one cable leading away from the circuit board, without the structural dimensions of the image pick-up module being increased due to that strain relief.

SUMMARY OF THE INVENTION

The invention achieves this object with respect to the before-mentioned image pick-up module by the fact that the image sensor is arranged on one side of the circuit board opposite the third section.

Instead of bonding the circuit board to the image sensor so that the image sensor comes to lie on the third section of the circuit board and the circuit board is open on the side opposite the image sensor, as described for the image pick-up module known from U.S. Pat. No. 5,220,198, it is provided by the invention that the circuit board is bonded to the image sensor by arranging the image sensor at the end of the circuit board opposite the third section so that the third section forms a bottom opposite the image sensor. This arrangement opens up the advantageous possibility to implement a strain relief device for the at least one cable leading away from the circuit board. The third section can be used with advantage to provide strain relief for the cable system. Another advantage of the configuration of the image pick-up module according to the invention consists in that strain relief can be implemented on the third section without increasing the circumferential dimensions of the image pick-up module beyond the circumference of the image sensor, because the third section is arranged between the first and the second section and does not, therefore, project beyond it. In addition, the third section can be used with advantage for the bonding function between the first and the second sections.

With respect to the method mentioned at the outset, it is further an object of the present invention to improve the before-mentioned method so as to facilitate the preassembly of the signal electronics on the circuit board and also bonding to the at least one cable.

The invention achieves this object with respect to the before-mentioned method by the fact that initially the circuit board has the form of a planar board blank comprising at least three sections that can be folded along flexible connecting sections, that the at least one cable is bonded to the board blank, that thereafter the board blank is folded in such a way that a third section is located between the first section and the second section, and that thereafter the image sensor is bonded to the circuit board at an end of the board opposite the third section.

According to the invention, therefore, once the signal electronics have been mounted on the board blank, one initially bonds the at least one cable to the circuit board, having the form of a planar board blank, which is especially easy due to the fact that the different contacts are easily accessible on the flat-lying circuit board. After the at least one or the several cables have been bonded to the planar board blank, the board blank is then folded along the flexible connecting sections so that the first, the second and the third sections of the at least three sections form the desired shape, whereafter the folded structure is bonded to the image sensor. The method according to the invention is, thus, especially well-suited for producing miniaturized image pick-up modules.

According to a preferred embodiment, the first and the second sections extend substantially in parallel one to the other, and the third section extends obliquely or crosswise to the first and second sections.

In the case of this embodiment of the circuit board, the board exhibits substantially the shape of a U. Since in this case the third section extends substantially crosswise to the at least one cable leading away from the circuit board, this embodiment of the circuit board provides the advantage that the third section is capable of effectively absorbing any tensile forces acting on the at least one cable, in the sense of a strain relief device.

Alternatively, it is, however, likewise preferred if the third section has a substantially V-shaped configuration.

This provides the advantage that the at least one cable leading away from the circuit board can be bonded to the outer surface of the V-shaped third section, which makes bonding of the cable to the circuit board especially easy. Further, it is also possible with this embodiment to provide strain relief measures on the outer surface of the third section of the circuit board, without increasing the outer circumference of the image pick-up module beyond the outer circumference of the image sensor. Another particular advantage resulting from this arrangement is seen in the especially short overall length that can be achieved for the entire image pick-up module.

It is also possible to provide that two legs of the V-shaped third section extend along a straight-line prolongation of the first and the second sections, respectively.

To say it in other words, the circuit board of this embodiment has generally the shape of a V, without any transition being noticeable between the first section and the third section, and the second section and the third section, respectively.

Alternatively, it is however also preferred if the first and the second sections extend substantially in parallel one to the other so that in this case the V-shaped third section, or more exactly its two converging legs, form an angled transition to the first and second sections, respectively.

According to another preferred embodiment, it is likewise preferred if the third section is curved in outward or inward direction. This, too, can be of advantage as regards ease of production and simple constructional design of the circuit board.

According to a further preferred embodiment, the at least one cable is bonded to an inner surface of the circuit board.

This provides the advantage that the at least one cable is arranged in the interior of the folded circuit board so that the cable, especially if a coaxial cable is used, or the cables, where a plurality of cables is used, do not increase the outer dimension of the image pick-up module. In the case of the before-mentioned method according to the invention, the board blank is then folded after the at least one cable has been bonded, so that the cable comes to lie inside the folded circuit board.

Alternatively, it is of advantage, especially when the third section is configured in the form of a V, if the at least one cable is bonded to an outer surface of the circuit board, especially to the outside of the V-shaped third section, as has been described before in connection with the configuration of the third section in the form of a V.

According to a further preferred embodiment of the image pick-up module, the third section comprises at least one passage for the at least one cable leading away from the circuit board.

The passage in the third section of the circuit board, that forms the bottom of the image pick-up module, provides the advantage, especially in the embodiment just mentioned, that the cable being bonded to the circuit board on its inside is guided past the third section without projecting laterally beyond the outer dimension of the circuit board and, thus, without increasing the outer dimension of the image pick-up module. In addition, the at least one passage may, advantageously, serve as strain relief, for example when the cable or the several cables are fixed in their positions in the at least one passage of the third section by corresponding measures, for example by clamps. While the passage may serve as passage for the entire cable system, there may also be provided several passages for the different cables or different cable bundles.

In the case of the method according to the invention, the at least one passage preferably is produced before the at least one cable is connected.

In this connection, it is further preferred if the at least one passage is formed as a marginal recess in the third section.

This feature provides the advantage that for bonding the at least one cable to the circuit board, the at least one cable can be positioned on the circuit board in flat stretched condition so that when the third section is then folded, it can be moved past the cable without any trouble into its final position, crosswise to the outgoing cable, without the cable forming an obstacle to the folding operation.

It is, however, also preferred if the at least one passage is configured as a substantially central opening in the third section.

Although this configuration requires that the at least one cable, before being connected, must be threaded through the board blank in its planar spread condition, this feature provides however the advantage that the at least one outgoing cable, or the cable bundle, can be guided off the circuit board centrally.

According to a further preferred embodiment of the image pick-up module, the interior of the circuit board, defined by the first, second and third sections, is filled with an electrically non-conductive filling compound.

This feature opens up a particularly favorable way of providing strain relief for the at least one outgoing cable, creating an intimate contact between the sections of the circuit board and the at least one outgoing cable, which connection is capable of safely withstanding even especially high tensile strains. Another advantage of this feature lies in the fact that strain relief is in this case implemented completely inside the circuit board so that the image pick-up module is not increased in dimension. In addition, the filling compound has the favorable effect of strengthening the overall structure.

The method of the invention thus provides that the interior of the folded circuit board, defined by the first, second and third sections, is filled up with a curing electrically non-conductive filling compound, whereafter the image sensor is bonded to the circuit board.

This permits strain relief to be implemented by an especially simple procedure since a curing filling compound can be introduced into the interior of the circuit board in its soft or even flowing condition, without any effort.

The filling compound used may be a curing resin, for example a two-component adhesive. The folded circuit board may be placed for this purpose in a mold or casing to prevent the filling compound from escaping before it has cured.

According to another preferred embodiment of the image pick-up module, the circuit board comprises a forth section arranged opposite the third section and accommodating the image sensor on its outer surface.

The forth section, therefore, advantageously serves as a planar support or carrying plate for the image sensor so that the latter can be connected with the circuit board in a mechanically safe manner, in addition to fastening it on the outer surface of the first and second sections via the bonding arrangement. Further, the forth section can, advantageously, accommodate additional components while being connected with the image sensor only mechanically and, normally, not electrically, if desired.

According to the method of the invention, where the circuit board is folded from a planar board blank, the board blank may also comprise the forth section, flexibly and integrally connected with one or more of the before-mentioned three sections, so that the assembly effort is not increased by that arrangement.

It is further preferred in this connection if the forth section comprises at least one electric component and/or at least one electric circuit-board conductor.

This arrangement provides the advantage that the forth section also provides the possibility of accommodating parts of the signal electronics so that there is, generally, more room available for the circuits and electronic components.

According to a further preferred embodiment, the circuit board comprises, in addition to the first section and the second section, one or two additional sections arranged on a longitudinal side of the circuit board.

This feature provides the advantage that the signal electronics of the circuit board can be entirely enclosed on all sides by sort of a casing and can thus be protected from damage. Another advantage of this feature is seen in the fact, in connection with filling the interior of the circuit board with a curing filling compound, that by enclosing the interior of the circuit board on all sides, the filling compound can be largely prevented from escaping before curing, even without any additional encasing measures.

According to a further preferred embodiment, the circuit board is provided on its outer surface with recesses for bonding of the image sensor.

Since, usually, the contact fingers of the image sensor are bonded to the circuit board on the outer surfaces of the circuit board, this feature provides the advantage that the contact fingers can be placed in the recesses with the result that the outer dimensions are not increased by the electric bond between the image sensor and the circuit board.

According to a further preferred embodiment, the third section of the circuit board comprises at least one contact for bonding the cable leading away from the circuit board.

In connection with the embodiment where the circuit board comprises a bottom in the form of the third section, the latter can be used with advantage for bonding further cables or a shielding line for the entire cable, or a multi-core cable, respectively, in which case those cables can be bonded to the third section in similar strain-relieved fashion by corresponding measures.

According to another preferred embodiment, the third section of the circuit board comprises at least one electric circuit-board conductor for electrically connecting the first section and the second section.

This feature provides the advantage that the third section, in addition to fulfilling a strain-relief function, may serve to electrically connect the first and the second sections without any additional lines or connecting circuit boards being required for that purpose.

An especially preferred board blank, from which the circuit board is folded, is configured in such a way that the first section and the second section are flexibly connected via an additional section, but are arranged in spaced relationship at one and the same level, that the first section and the second section each serve for bonding at least one cable, and that the third section is flexibly connected to the additional section on the latter's end face.

A board blank configured in this way makes the preassembly of the signal electronics and, above all, the connection of a plurality of cables especially easy because it is thus possible to bond a cable bundle to each of the first and the second sections so that the cable bundles are spaced one from the other and will not obstruct each other, and because the subsequent folding operation, by which the circuit board is finished and given its final structure, is also rendered particularly easy, especially when the passages in the third section are formed as marginal recesses.

Instead of filling the interior of the circuit board, being defined by the first, second and third sections, with a filling compound, as mentioned before, it may also be provided to fill that interior with a contact body which on the one hand establishes contact with the first section and the second section and, on the other hand, embodies a plug-in connector system for the at least one outgoing cable. Preferably, such a plug-in connector implemented within the contact body is a microconnector system. Due to the progress achieved in microtechnology, it is possible today to produce such microconnector systems.

Further advantages are evident from the description below and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description which follows. In the drawings.

DETAILED DESCRIPTION OF THE INVENTION

Figure 1:
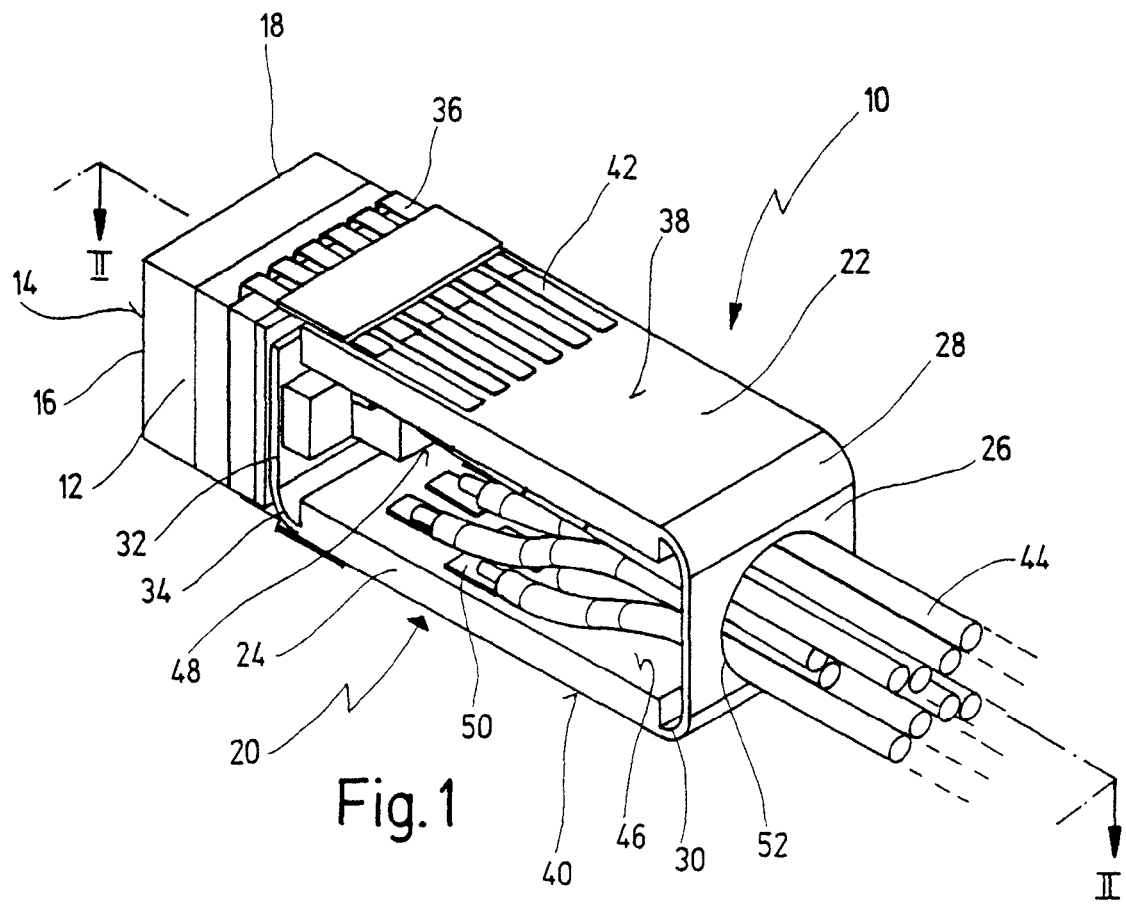
FIG. 1 shows a perspective view of an image pick-up module according to a first embodiment.

FIG. 1 shows an electronic image pick-up module, indicated generally by reference numeral 10. The image pick-up module 10 is installed, for example, in the distal tip of an endoscope shaft not shown. As illustrated in FIG. 1, the image pick-up module 10 is ready for being installed, which means that the image pick-up module 10 will not be enclosed in an additional casing; as will be shown in the description that follows, there is no need for such an additional enclosure in the case of that embodiment of the image pick-up module 10 according to the invention since all sensitive and, possibly, strain-loaded elements are safely protected.

The image pick-up module 10 comprises an image sensor 12 with an image pick-up surface 14.

The image sensor 12 is an electric image sensor in CCD or CMOS technology. Such image sensors are commercially available. Image sensors of this kind constitute optoelectronic converters, which means that light, which is received via the image pick-up surface 14 pixel for pixel, is converted to electric signals by the image sensor 12.

Specifically, the image sensor 12 is a miniaturized image sensor whose outer edges 16 and 18 each have a length of about 4 mm, to mention one example only. In addition, the image sensor 12 is designed without a casing in what is known as TAB technology, with the contacts projecting laterally from the sensor. The design of the image sensor 12 without a casing further contributes toward realizing a space-saving structure of the image pick-up module.

The image pick-up module 10 further comprises a circuit board indicated generally by reference numeral 20. The circuit board 20 is formed entirely in one piece.

The circuit board 20 comprises a first section 22 and a second section 24. The first section 22 and the second section 24 extend in spaced relation to and substantially parallel one to the other, and substantially perpendicularly to the image sensor 12 or the image pick-up surface 14.

Further, the circuit board comprises a third section 26 extending crosswise to the first section 22 and crosswise to the second section 24, and substantially parallel to the image sensor 12 or the image pick-up surface 14. The third section 24 connects the first section 22 and the second section 24 to form a single piece in this case.

The third section 26 is integrally connected with the first section 22 via a first flexible connecting section 28, and with the second section 24 via a second flexible connecting section 30. As can be seen in FIG. 1, the first section 22 and the second section 24 have a thickness greater than the thickness of the third section 26 and the connecting sections 28 and 30.

The circuit board 20 further comprises a forth section 32 which is flexibly and integrally connected with the second section 24, via a third flexible connecting section 34. The forth section 32 extends substantially parallel to the third section 26 and is arranged opposite the latter on the other end of the circuit board 20.

The first section 22, the second section 24 and the third section 26 exhibit together the shape of a U.

The circuit board 20, or more specifically the first section 22 and the second section 24 of the circuit board 20, accommodate in this case microelectronic components, electric circuit-board conductors, printed electric circuits, and the like, constituting the signal electronics of the image sensor 12.

The image sensor 12 is electrically bonded to the circuit board 20, more specifically to the first section 22 and the second section 24. The image sensor 12 is provided to this end with a plurality of contact fingers 36, in the illustrated embodiment with five contact fingers 36 and, opposite the latter, additional five contact fingers, which project to the outside on opposite sides of the image sensor 12. Bonding of the image sensor 12 to the circuit board 20 is effected on an outer surface 38 of the first section 22 or an outer surface 40 of the second section 24 of the circuit board 20, opposite the outer surface 38, for which purpose corresponding contact areas 42 are provided on the outer surfaces 38 and 40. The contact areas 42 are arranged in recesses in the outer surfaces 38 and 40 so that the contact fingers 36 of the image sensor 12 come to lie in these recesses and do not, consequently, project laterally to the outside.

Further, at least one electric cable 44 leading away from the circuit board 20 is bonded to the circuit board 20; in the illustrated embodiment a cable system comprising a plurality of cables 44 leads away from the circuit board 20. The cables 44 lead to a remote electronic signal-processing and/or control system, not shown, for the image pick-up module 10, and may be bundled in a jacket, for example a plastic jacket.

The electric connection of the cables 44 is realized on the inner surfaces 46 and 48 of the second section 24 or the first section 22, respectively, of the circuit board 20, for which purpose the inner surfaces 46 and 48 are provided with corresponding contact areas 50 which, just as the contact areas 42 on the outer surfaces 38 and 40, are arranged in corresponding recesses.

Since the third section 26 is arranged opposite the image sensor 12, as mentioned before, the third section 26 forms a bottom which permits a strain relief device to be implemented without any additional space-consuming measures that would increase the outer dimension of the image pick-up module 10.

In the first place, a passage 52 is provided in the third section 26 in the form of a substantially central opening through which the cables 44 are passed. Initial strain relief is achieved by passing the cables 44 through the passage 52 due to the fact that relative displacement between the cables in the passage 52 in lengthwise direction is hindered by the frictional grip of the different cables 44 on the edge of the passage 52 and between the different cables 44.

In the case of the image pick-up module 10, a strain relief device, effective under particularly high strain conditions, is achieved by filling the interior of the circuit board 20, which is defined by the first section 22, the second section 24 and the third section 26 and in which the ends of the cables 44 are bonded to the circuit board 20, with a non-conductive filling compound that achieves an especially intimate connection between the cables 44 and the circuit board 20 due to the fact that the filling compound fills up all, or almost all, of the remaining cavities inside the circuit board. The filling compound may consist, for example, of a cured resin, for example a two-component adhesive which is not conductive electrically.

As can further be seen in FIG. 1, the image sensor 12 is arranged on the forth section 32 of the circuit board 20 so that the forth section 32 serves as an additional mount for the image sensor 12 on the circuit board 20.

Figure 2:
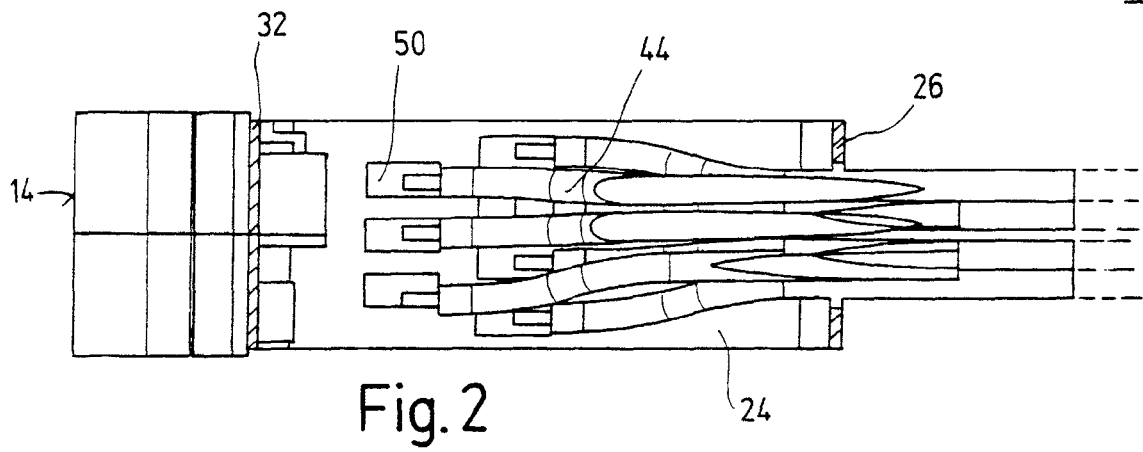
FIG. 2 shows a sectional view taken along line II-II in FIG. 1.
Figure 3:
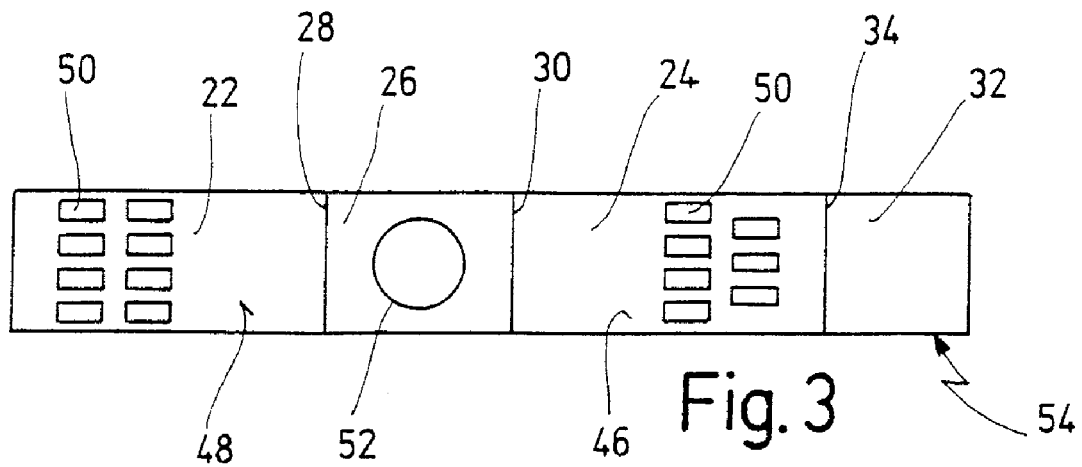
FIG. 3 shows a top view of a board blank from which is folded the circuit board of the image pick-up module illustrated in FIGS. 1 and 2.

FIG. 3 shows a board blank 54 from which the circuit board 20 of the image pick-up module 10 illustrated in FIGS. 1 and 2 has been folded.

A method for assembling the image pick-up unit 10 operates as follows. Starting out from the planar board blank 54, one initially applies the microelectronic components, conductors and the like, on the first section 22 and the second section 24, i.e. the surfaces that later become the inner surfaces 48 and 46 (the surface shown in the top view of FIG. 3). With the board blank 54 still in the unfolded, i.e. its planar condition the cables 44 are then bonded to the first section 22 and the second section 24, in the contact areas 50. Before, the corresponding cable ends of the cables 44 were passed through the passage 52 provided in the third section 26 of the circuit board 20 in the form of the substantially central opening, produced in the third section 26 of the board blank 54 prior to the bonding process.

Once all cables 44 have been bonded to the board blank 54, the sections 22, 24, 26 and 32 are then folded to obtain the shape of the circuit board 20 illustrated in FIG. 1. Thereafter, the interior of the circuit board 20 is filled with a curing filling compound which, in the cured condition, strengthens the entire structure of the image pick-up module 10 and ensures additional strain relief for the cables 44. Finally, the image sensor 12 is bonded to the circuit board 20.

The third section 26 may likewise comprise electric circuit-board conductors for electrically connecting the first section 22 and the second section 24 of the circuit board 20.

Figure 4:
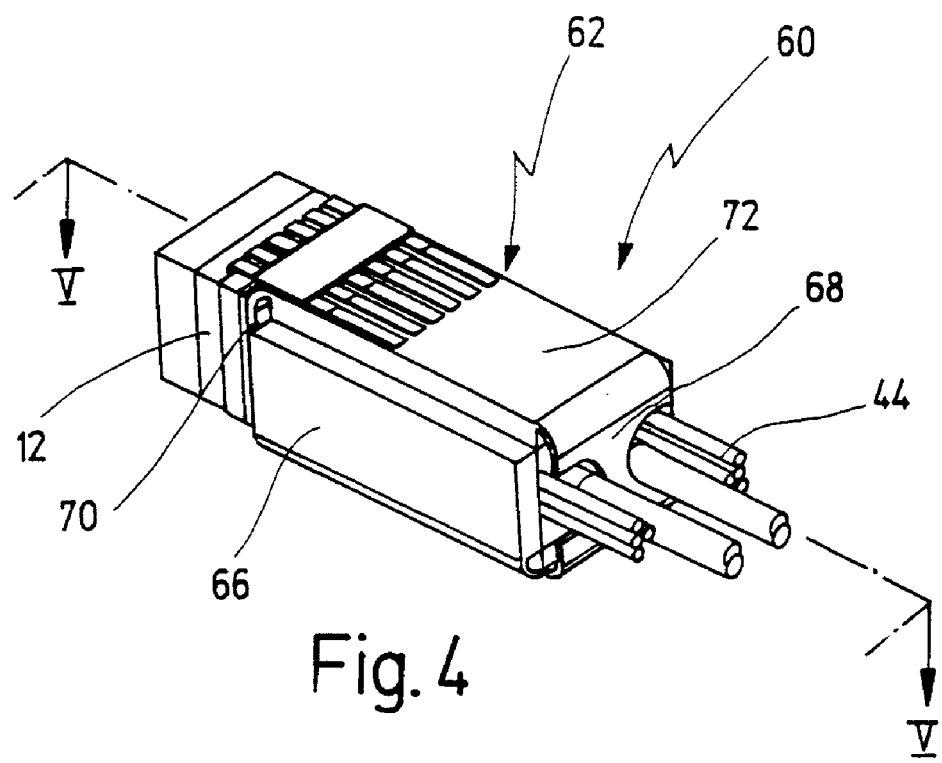
FIG. 4 shows a perspective view of an image pick-up module according to a second embodiment.
Figure 5:
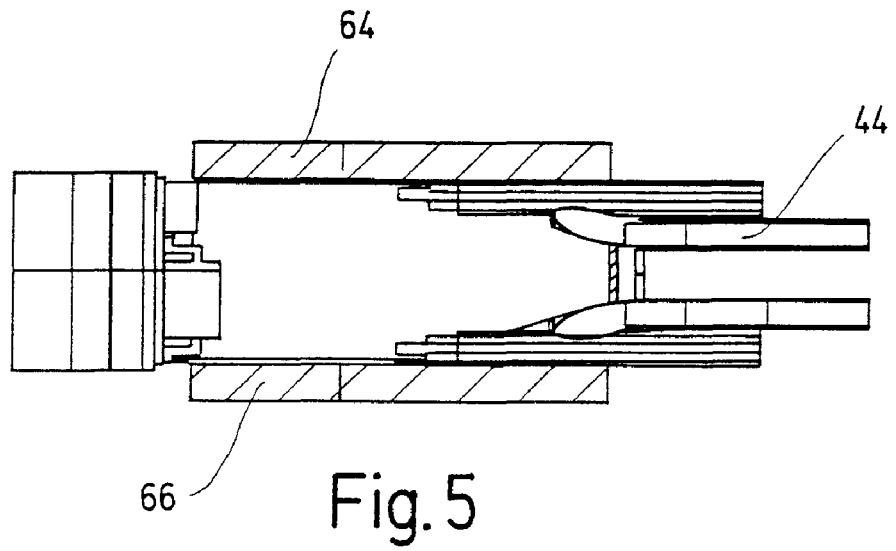
FIG. 5 shows a sectional view taken along line V-V in FIG. 4.

FIGS. 4 and 5 show another embodiment of an image pick-up module 60. In the description that follows, reference will be made mainly to the differences from the embodiment previously described, while features not mentioned in that description are identical or similar to corresponding features of the image pick-up module 10.

In this embodiment, the image sensor 12 is bonded to a circuit board 62 comprising a first section 64, a second section 66 and a third section 68 that together form the shape of a U. The circuit board 62 is likewise formed entirely as a single piece. The third section 68 is arranged opposite the image sensor 12. A forth section 70, corresponding to the forth section 32 of the circuit board 20 in FIGS. 1 to 3, serves again as mechanical mount and/or support for the image sensor 12.

In addition to the before-mentioned sections, the circuit board 62 comprises, however, a fifth section 72 and a sixth section 74 which connect the first section 64 and the second section 66 in the form of lateral walls.

The image sensor 12 is bonded in this case to the sections 72 and 74, while the cables 64 are bonded to the first section 64 and the second section 66.

Consequently, the circuit board 62 forms a casing with walls on all sides, in which the signal electronics and the bonds of the cables 44 are safely protected. The interior space of this embodiment may likewise be filled with a cured filling compound in order to provide for additional strain relief of the cables 44.

Figure 6:
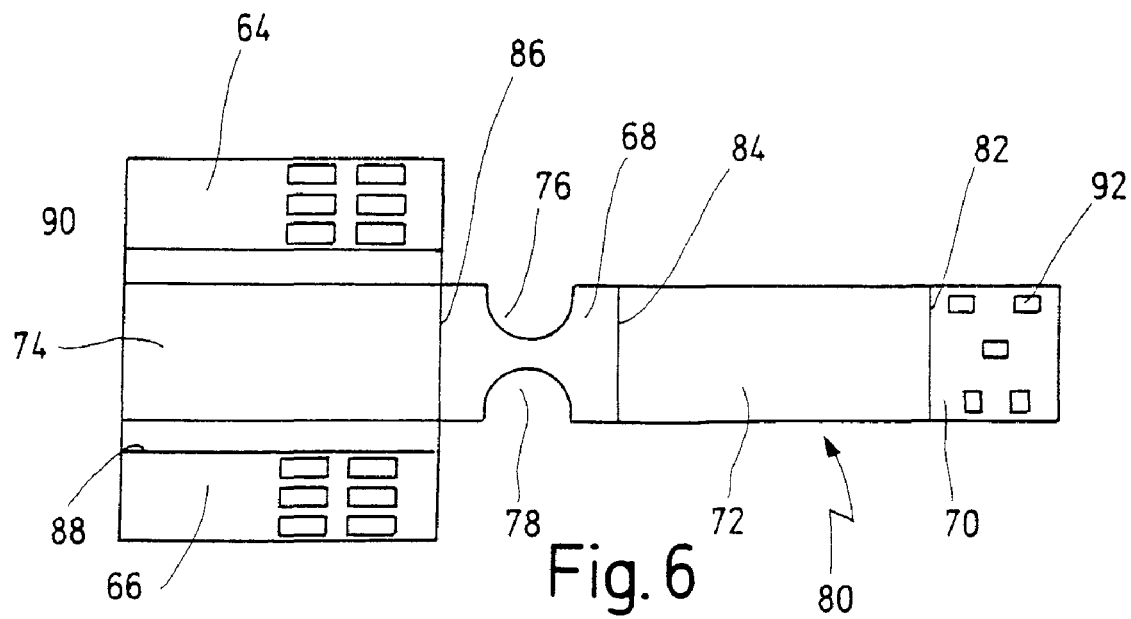
FIG. 6 shows a top view of a board blank from which has been folded the circuit board of the image pick-up module illustrated in FIGS. 4 and 5.

The third section 68 comprises at least one passage for the cables 44, in the embodiment shown two passages 76 and 78, which are, however, not configured as a central opening but rather as marginal recesses provided in the edge of the third section 68, as can be seen in FIG. 6. During assembly of the image pick-up module 60, this provides the advantage that the cables 44 need not be threaded through an opening before being bonded to the first section 64 and the second section 66.

A planar board blank 80, from which the circuit board 62 is folded, is illustrated in FIG. 6.

In this case, the first section 64 and the second section 66 of the board blank 80 are arranged one parallel to the other and at the same level, and are connected one with the other in spaced relationship by the further section 74. The third section 68 is connected with the further section 74 on its end face.

In the case of this board blank 80, bonding of the cables 44 to the first section 64 and to the second section 66 is particularly easy because the cables 44 can be arranged in two parallel lines, with their longitudinal extension lying in the plane of the board blank 80, and need not be passed through an opening before. Thus, the cables 44 can be placed on the working support in fully stretched condition, i.e. without any bend. After completion of the bonding process, the different sections 64 to 74 can then be folded along flexible connecting sections 82 to 90 so as to obtain the structure of the circuit board 62 illustrated in FIG. 4, during which operation the third section 68, with the passages 76 and 78, can be folded easily without being obstructed by the two cable bundles 44.

It is further provided in this embodiment that the forth section 70 of the circuit board 62 is likewise equipped with contacts 92.

Figure 7:
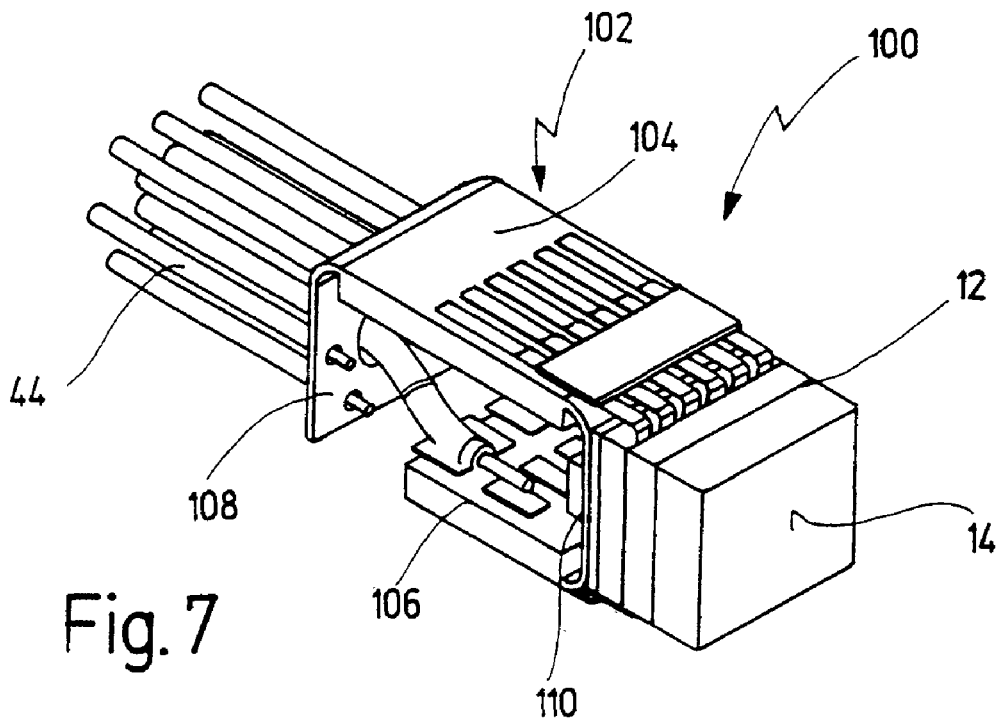
FIG. 7 shows a perspective view of an image pick-up module according to a third embodiment.
Figure 8:
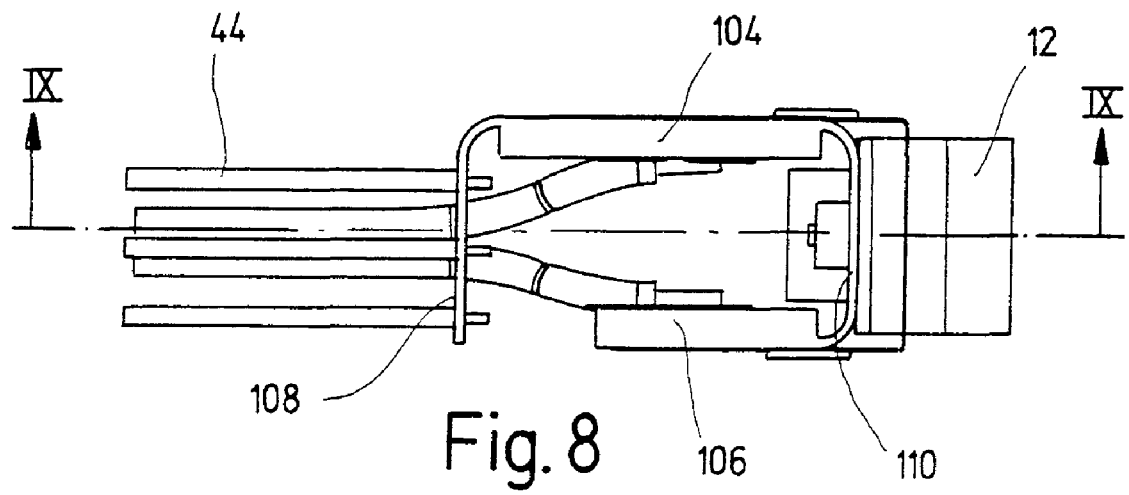
FIG. 8 shows a side view of the image pick-up module illustrated in FIG. 7.
Figure 9:
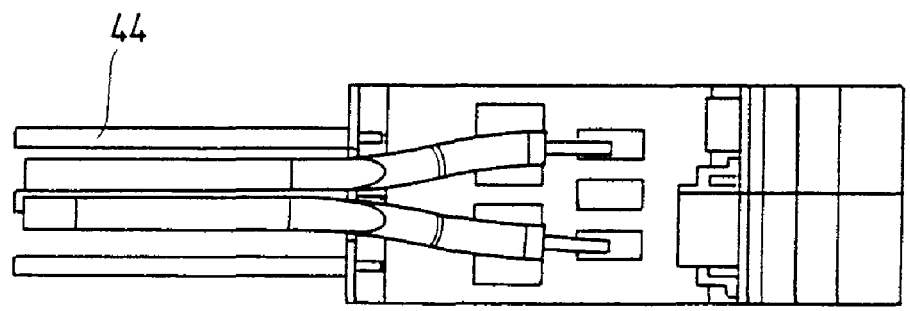
FIG. 9 shows a sectional view taken along line IX-IX in FIG. 8.

FIGS. 7 to 9 show an image pick-up module 100 according to another embodiment of the invention that differs from the previously described embodiments by certain individual features of a circuit board 102.

Figure 10:
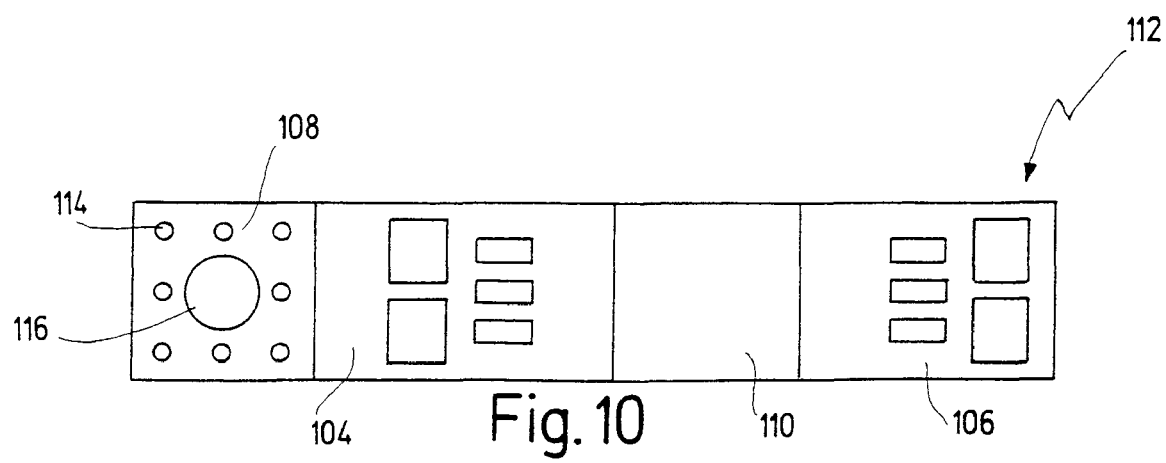
FIG. 10 shows a top view of a board blank from which has been folded the circuit board of the image pick-up module illustrated in FIGS. 7 to 9.

The circuit board 102 comprises a first section 104, a second section 106, a third section 108 and a forth section 110, all of them being connected to form a single piece, with the first section 104, the second section 106 and the third section 108 forming the shape of a U. In contrast to the two previous embodiments, there is however no direct connection between the third section 108 and the second section 106. A corresponding planar board blank 112, from which the circuit board 102 is folded to obtain the structure illustrated in FIGS. 7 and 8, is illustrated in FIG. 10.

The third section 108 of the circuit board 102 offers additional bonding possibilities for part of the cables 44, for which purpose additional openings 114 are provided in the third section 108. A passage 116 for the remaining cables 44 is again provided in the third section 108 so that that part of the cables 44 can be bonded to the inner surfaces of the sections 104 and 106 of the circuit board 102.

Figure 11:
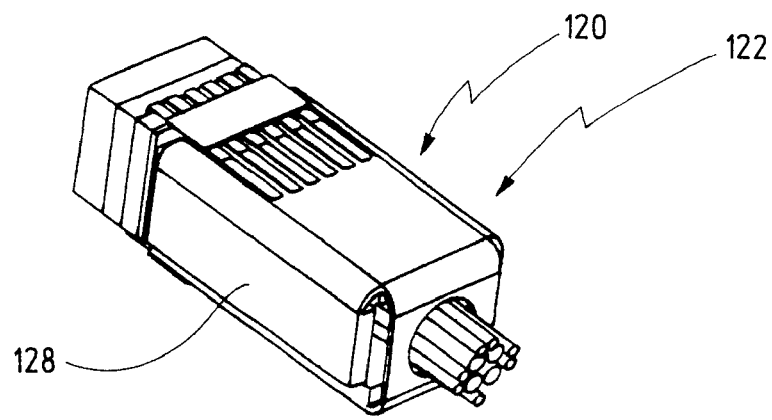
FIG. 11 shows a perspective view of an image pick-up module according to a forth embodiment.
Figure 12:
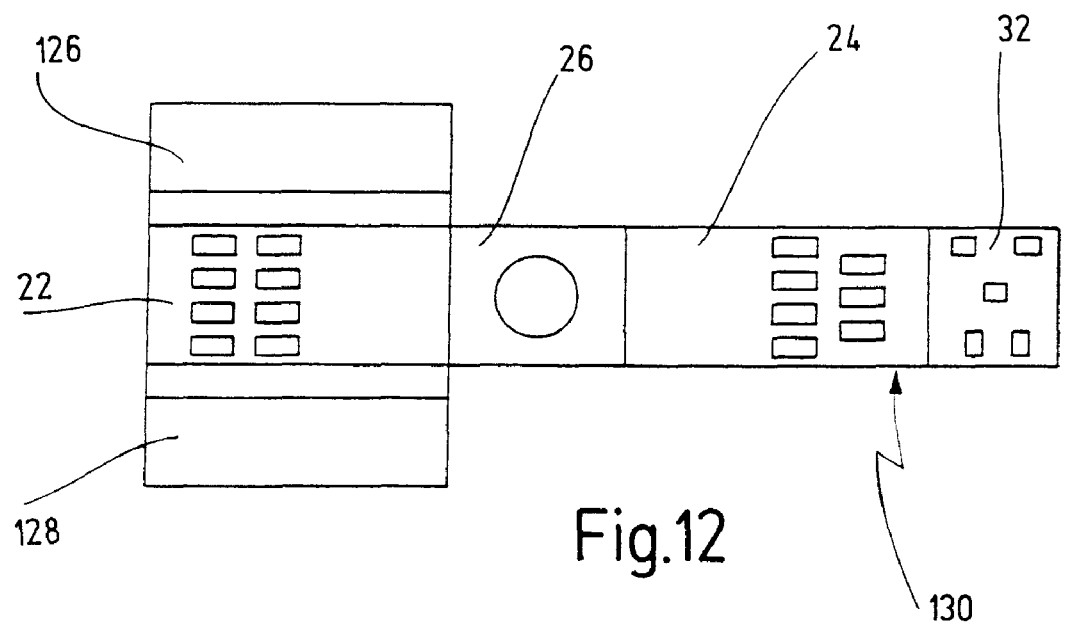
FIG. 12 shows a top view of a board blank from which has been folded the circuit board of the image pick-up module illustrated in FIG. 11.

Finally, a forth embodiment, being very similar to the embodiment illustrated in FIGS. 1 to 3 and constituting an extension of that embodiment, is illustrated in FIGS. 11 and 12. According to this embodiment, an image pick-up module 120 comprises a single-piece circuit board 122 having, in addition to the first four sections 22, 24, 26, 32 shown in FIG. 1, a fifth section 124 and a sixth section 128, which are integrally formed with the first section 22, as shown in FIG. 12, and which form a lateral termination of the circuit board 122. A corresponding planar board blank 130, from which the circuit board 122 is folded, is illustrated in FIG. 12.

Figure 13:
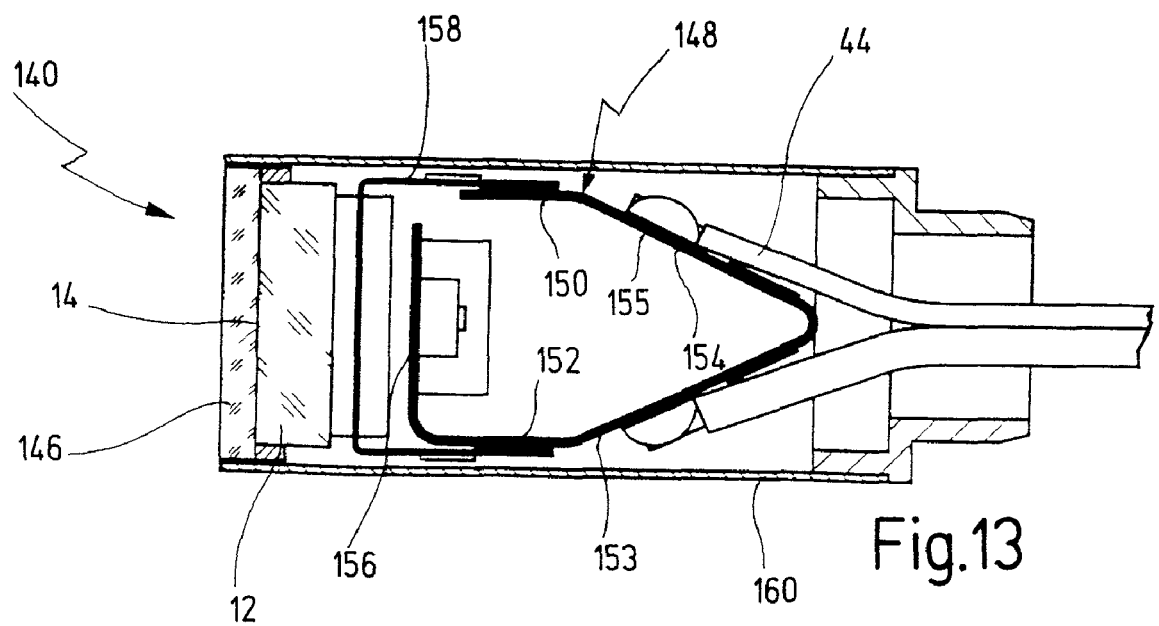
FIG. 13 shows a longitudinal section through an image pick-up module according to a fifth embodiment.

FIG. 13 shows yet another embodiment of an image pick-up module 140 which differs from the embodiments previously discussed especially by the following features:

The image pick-up module 140 comprises a circuit board 148 having, as before, a first section 150 and a second section 152 as well as a third section 154.

In contrast to the previously described third sections, the third section 154 exhibits, however, the shape of a V. The third section 154 has a first leg 153 and a second leg 155 converging toward the end opposite the image sensor 12.

The first leg 153 extends obliquely to the second section 152, or forms an angle with the latter, while the second leg 155 forms an angle with the first section 150. Alternatively, it may however be provided that the first leg 153 forms a straight-line prolongation of the second section 152, which means that in this case the second section 152 also extends obliquely to the image sensor 12, and similarly the second leg 155 of the third section 154 may form a straight-line prolongation of the first section 150. In this case, the entire circuit board 148 would then exhibit the shape of a V.

As can be seen in FIG. 13, the at least one cable 44 is bonded to the circuit board 148 on an outer surface thereof, more specifically on an outer surface of the V-shaped third section 154. As illustrated in FIG. 13, bonding the at least one cable 44 to the outer surface of the V-shaped third section 154 does not in this case increase the circumference of the image pick-up module 140 beyond the outer circumference of the image sensor 12. However, it may also be provided to bond the at least one cable 44 to the circuit board 148 on an inner surface of the latter, as has been described in connection with the previously discussed embodiments.

In addition, a strain relief device (not shown) may be provided in the area of the outer surface of the third section 154 of the circuit board 148, for example in the form of clamps or the like. Another strain relief measure may consist in filling the interior of a casing 160, in which the image pick-up module 140 is arranged, with a curing filling compound.

The circuit board 148 likewise comprises a forth section 156 carrying, or intended to carry, further electric or electronic components. Contact fingers 158, through which the image sensor 12 is bonded to the outer surface of the circuit board 148, are likewise shown in FIG. 13. A glass cover 146 closes off the distal end of the casing 160 in front of the image sensor 12.

The overall length of the image pick-up module 140 is shorter than that of the previously discussed embodiments. The previous embodiments show that a great number of modifications is possible within the scope of the present invention, with all such modifications offering the advantage of providing strain relief for the cables leading away from the circuit board, without increasing the outer dimensions of the respective image pick-up module; this is achieved by the third section at the bottom of the circuit board.

What is claimed is:
1. An image pick-up module comprising:
an electronic image sensor;
a single-piece circuit board which is electrically bonded to said image sensor, said circuit board having at least four sections, with a first section and a second section extending in spaced relation one to the other and obliquely or crosswise to said image sensor and a third section being arranged between the first and the second sections, a fourth section arranged opposite said third section;

at least one cable electrically bonded to said circuit board and leading away from said circuit board;

said image sensor being arranged on top of said fourth section of said circuit board opposite said third section, said fourth section comprising at least one electronic component arranged on a side of said fourth section opposite said image sensor.

2. The image pick-up module of claim 1, wherein said first and second sections extend substantially in parallel one to the other, and said third section extends obliquely or crosswise to said first and second sections.

3. The image pick-up module of claim 1, wherein said third section is curved.

4. The image pick-up module of claim 1, wherein said at least one cable is bonded to an inner surface of the circuit board.

5. The image pick-up module of claim 1, wherein said at least one cable is bonded to an outer surface of said circuit board.

6. The image pick-up module of claim 1, wherein said third section comprises at least one passage for said at least one cable leading away from said circuit board.

7. The image pick-up module of claim 6, wherein said at least one passage is configured as a marginal recess in said third section.

8. The image pick-up module of claim 1, wherein said third section comprises at least one passage for said at least one cable leading away from said circuit board, wherein said at least one passage is configured as a substantially central opening in said third section.

9. The image pick-up module of claim 1, wherein an interior of said circuit board, defined by said first, second and third sections, is filled with an electrically non-conductive feeling compound.

10. The image pick-up module of claim 1, wherein said circuit board comprises, in addition to said first section and said second section, at least one additional section arranged on one longitudinal side of said circuit board.

11. The image pick-up module of claim 1, wherein said circuit board is provided on its outer surface with recesses for bonding of said image sensor.

12. The image pick-up module of claim 1, wherein said third section of said circuit board comprises at least one contact for bonding said cable leading away from said circuit board.

13. The image pick-up module of claim 1, wherein said third section of said circuit board comprises at least one electric circuit-board conductor for electrically connecting said first section and said second section.

14. The image pick-up module of claim 1, wherein said circuit board is folded from a planar board blank comprising at least said integrally formed first, second and third sections.

15. The image pick-up module of claim 14, wherein said first section and said second section of said board blank are flexibly connected via an additional section, but are arranged in spaced relationship at one and the same level, wherein said first section and said second section each serve for bonding said at least one cable, and wherein said third section is flexibly connected to said additional section on an end face of said additional section.

* * * * *